United States Patent [19]

Nakajima

[11] Patent Number: 4,759,346
[45] Date of Patent: Jul. 26, 1988

[54] ENDOSCOPE DEVICE

[75] Inventor: Shigeru Nakajima, Hachioji, Japan

[73] Assignee: Olympus Optical Co., Ltd., Tokyo, Japan

[21] Appl. No.: 15,470

[22] Filed: Feb. 17, 1987

[51] Int. Cl.[4] .............................................. A61B 1/06
[52] U.S. Cl. .......................................... 128/6; 358/98
[58] Field of Search .......................... 128/4, 6; 358/98

[56] References Cited

U.S. PATENT DOCUMENTS 4,539,586 9/1985 Danna et al. .......................... 358/98
4,667,229 5/1987 Cooper et al. ....................... 128/6 X Primary Examiner—William H. Grieb
Attorney, Agent, or Firm—Armstrong, Nikaido, Marmelstein & Kubovcik

[57] ABSTRACT

This endoscope device is provided with two kinds of electronscopes different at least in the length of the insertion part and each housing a solid state imaging device on the tip side of the insertion part and a camera controlling unit making the respective electronscopes fittable and housing a means of impressing driving pulses for reading out signals on said solid state imaging device and a video signal processing means taking in and processing the output signal read out. The length of the signal cable electrically connecting the above mentioned solid state imaging device and camera controlling unit in each electronscope is made equal to that in the other electronscope.

17 Claims, 10 Drawing Sheets

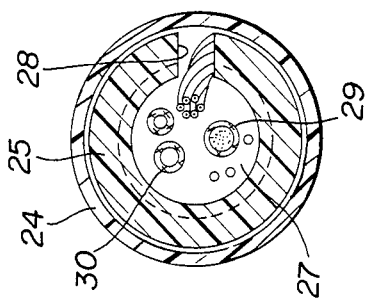
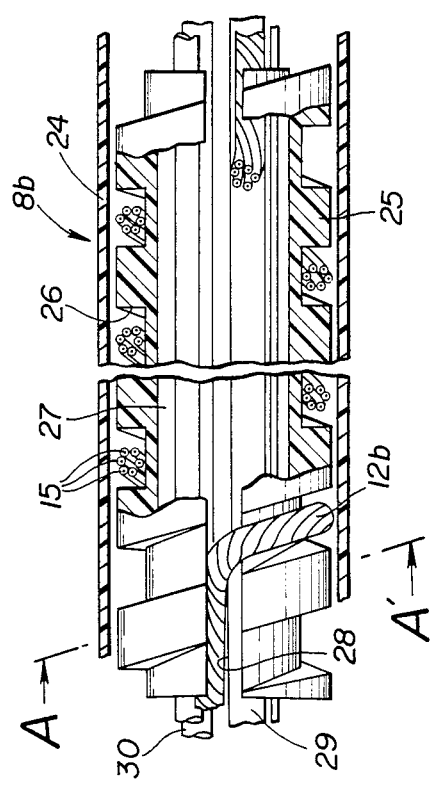
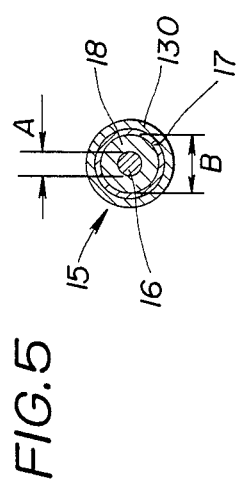

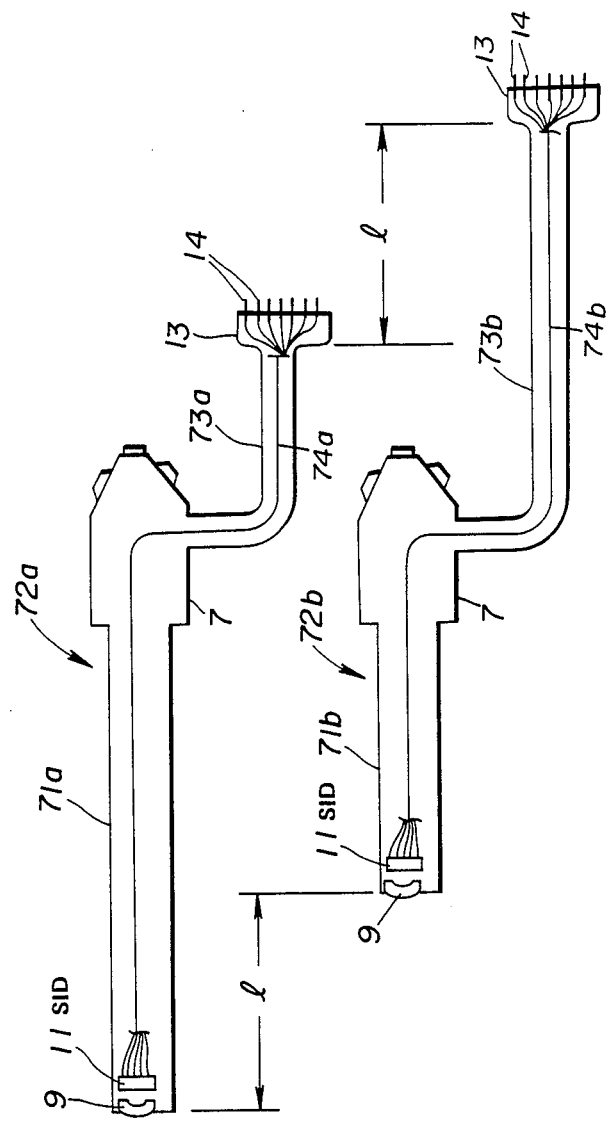

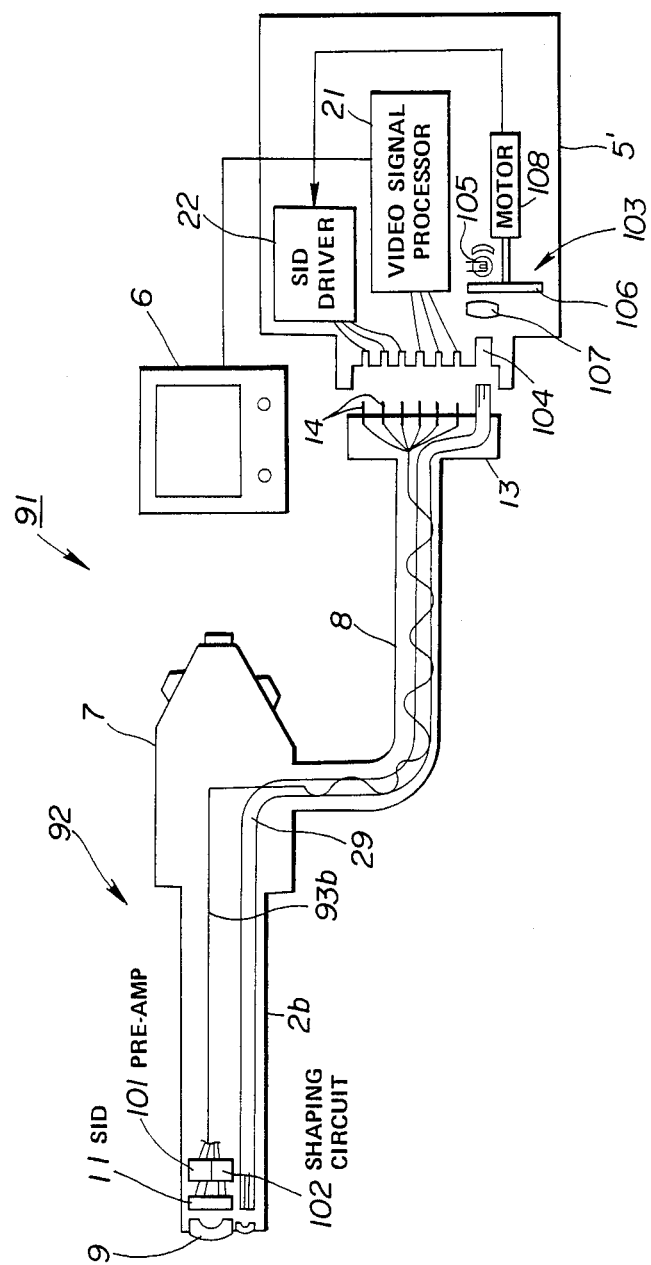

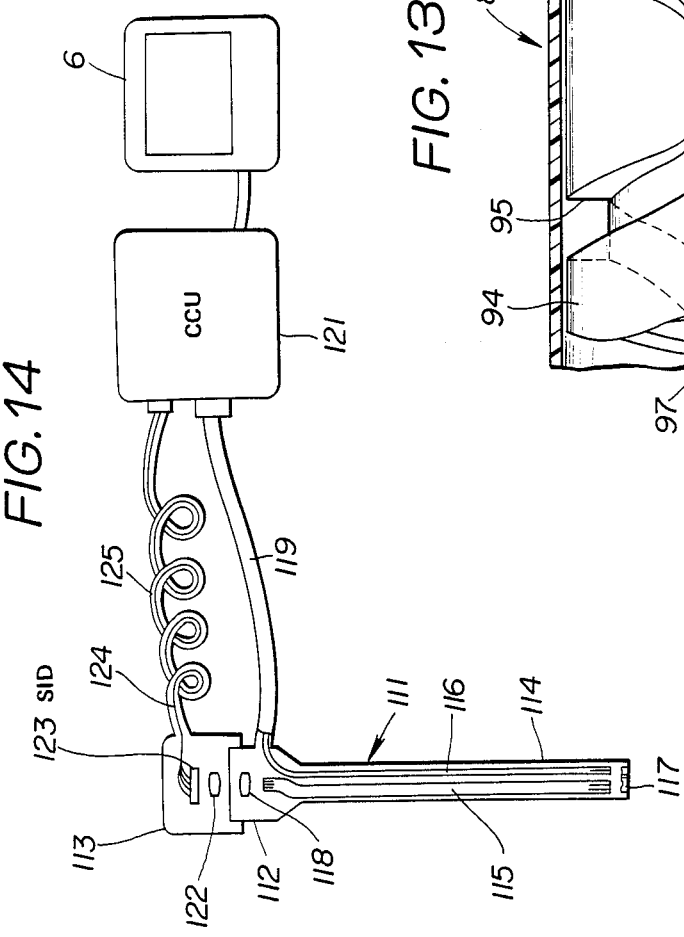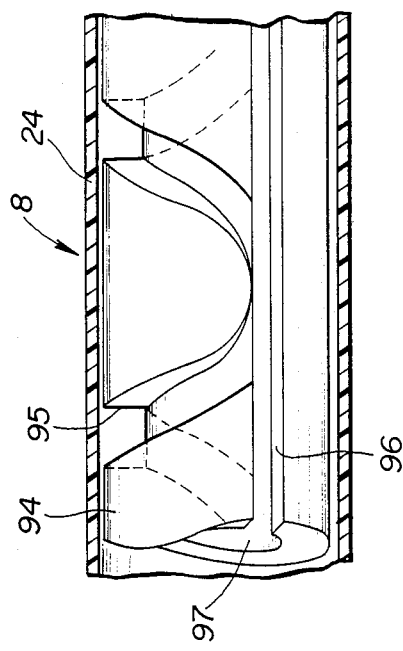

4,759,346

ENDOSCOPE DEVICE

BACKGROUND OF THE INVENTION

Field of the Invention and Related Art Statement

This invention relates to an endoscope device wherein the length of a signal cable for a solid state imaging device used in an imaging means of each electronscope is made equal to that of the other electronscope.

Recently, instead of an optical endoscope also called a fiberscope wherein an optical image formed by an objective in the tip part of an insertion part is transmitted to the holding side by an image guide formed of an optical fiber bundle, there has been used an electronic endoscope, also called an electronendoscope or electronscope, hereinafter, wherein an optical image formed by an object is photoelectrically converted to an electric signal by a solid state imaging device (referred to hereinafter as an SID of a charge coupled element referred to hereinafter as a. The electric signal or the like is transmitted to the holding side where the signal is fed to a video processor and the object image is displayed by a color monitor connected to the video processor.

In the above mentioned electronscope, the length of the insertion part for insertion inserted into a body cavity or pipe cavity is different depending on the uses. Therefore, the length of a signal cable inserted to the video processor, or a camera controlling unit, through the insertion part and a universal cord extended from the rear end side of the insertion part are also different.

When the length of the above mentioned signal cable is different, the resistance value of the entire signal cable is different. Therefore, the output gain of the SID is different. The S/N fluctuates and the impedance of the cable end part is different. Therefore, in case the cable is connected at the end to the camera controlling unit, the waveform by the reflection is disturbed, the delay amount of the SID driving pulses from the camera controlling unit is different and the delay amount of the video output signal is different. Therefore, in the prior art example disclosed, for example, in U.S. Pat. No. 4,539,586, a matching circuit is built-in within a connector of each electronscope to regulate the output gain of the SID and the impedance to prevent the disturbance of the waveform.

In the above mentioned prior art example, there are defects in that a matching circuit is necessary for each electronscope and that the matching must be adjusted for each electronscope. Therefore, the number of component parts is large and the production cost is high. In the case of the products, it is difficult to keep the fluctuation of the characteristics within a fixed range and to provide products within a fixed standard.

OBJECTS AND SUMMARY OF THE INVENTION

An object of the present invention is to provide an endoscope device wherein parts to be adjusted are few.

Another object of the present invention is to provide an endoscope device wherein fluctuations of products are few and a fixed quality can be guaranteed.

Further another object of the present invention is to provide an endoscope device wherein the component parts are few and the cost can be made low.

In the present invention, the length of a signal transmitting cable between a solid state imaging device arranged on the tip side of an insertion part and a camera controlling means containing a signal reading driving pulse producing means for such solid state imaging device and an image signal processing means for processing the read-out output signal to produce an image signal in each electronscope is made equal to that in the other electronscope to eliminate any unfavorable influence produced in case the cable length is different.

BRIEF DESCRIPTION OF THE DRAWINGS

FIGS. 1 to 5 relate to the first embodiment of the present invention.

FIG. 1 is a schematic view showing the entire system of an endoscope device of the first embodiment of the present invention.

FIG. 2 is a sectioned side view showing a signal cable as inserted through a universal cord of an electronscope having a short insertion part.

FIG. 3 is a sectioned view on line A—A' in FIG. 2.

FIG. 4 is a sectioned side view showing a signal cable as inserted through a universal cord of an electronscope having a long insertion part.

FIG. 5 is a sectioned view of a signal line forming a signal cable.

FIG. 10 is an explanatory view showing an electronscope in the sixth embodiment of the present invention.

FIG. 12 is a schematic formation view of the eighth embodiment of the present invention.

FIG. 13 is a side view showing a signal cable inserting side tube through a universal cord in the eighth embodiment of the present invention.

FIG. 14 is a schematic formation view of the ninth embodiment of the present invention.

DETAILED DESCRIPTION OF PREFERRED EMBODIMENTS

Figure 1:
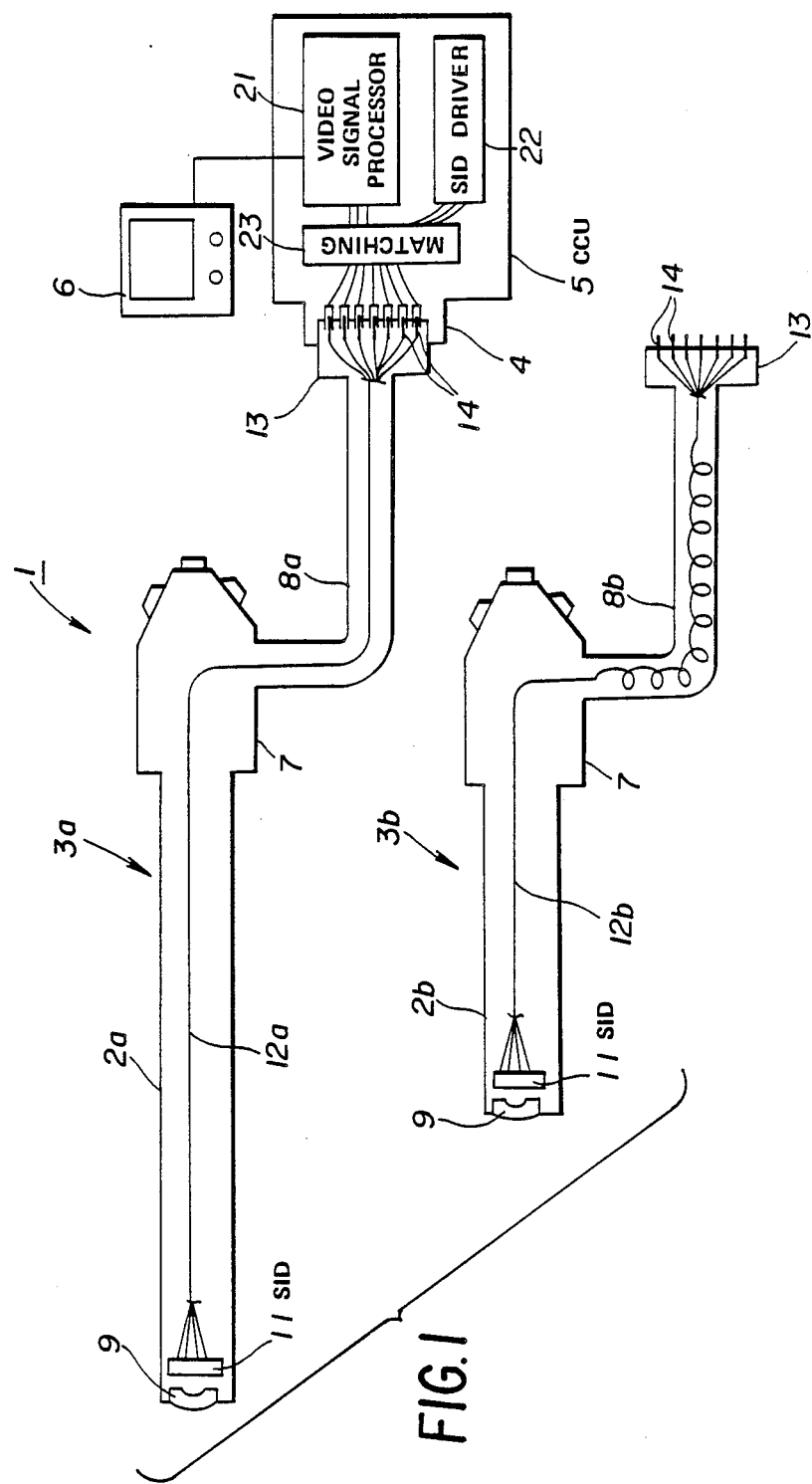

As shown in FIG. 1, an endoscope device 1 of the first embodiment comprises electronscopes 3a and 3b having respective insertion parts 2a and 2b of different length, a camera including unit (or video processor unit) 5 having a connector receiver 4 for connection to the respective electronscopes 3a and 3b and containing a signal processing means and a color monitor 6 for receiving and color-displaying a video signal transmitted from the camera controlling unit (mentioned as a CCU hereinafter).

The above mentioned electronscope 3a (or 3b) comprises an insertion part 2a (or 2b) elongated for insertion into a body cavity or pipe cavity, a wide operating part 7 provided as connected to the rear end of the insertion part 2a (or 2b) and a universal cord 8a (or 8b) extended out of the operating part 7.

An lens 9 for forming an image of an object is arranged on the tip side of the above mentioned insertion part. An imaging surface (light receiving surface) of a solid state imaging device (mentioned as an SID hereinafter) 11 of a CCD, or the like, is positioned at the focal plane of lens 9. An imaging means is formed by lens 9 and SID 11. That is to say, an optical image of the object is formed on the imaging surface of the SID 11 and is photoelectrically converted to an electric signal.

A signal cable 12a (or 12b) comprising a plurality of signal lines for driving pulse transmission impressing driving pulses for reading out signals on the SID 11, for output signal transmission transmitting output signals read out of the SID and for feeding electric power to the SID is connected at one end to each SID 11. The signal cable 12a (or 12b), inserted through the insertion part 2a (or 2b) of each electronscope 3a (or 3b) and through the universal cord 8, is connected at the other end to a plurality of pin-like terminals 14 in a connector 13 connected to the above mentioned connector receiver 4.

As shown in FIG. 5, a coaxial cable comprising an internal conductor 16, an external conductor 17, a dielectric member 18 interposed between both conductors 16 and 17 and an external insulating coating coating the external conductor 17 form the signal cables 12a and 12b within the above mentioned two electronscopes 3a and 3b.

If the diameters of the above mentioned internal conductor 16 and external conductor 17 are represented respectively be A and B and the specific dielectric constant of the dielectric member fitted between them is represented by K, the characteristic impedance $Z_o$ of this signal will be represented by $$Z_o = (138/\sqrt{K}) \log (B/A) [\Omega].$$

The signal cables 12a and 12b used within the above mentioned two electronscopes 3a and 3b are characterized by being equal to each other in the above mentioned characteristic impedance $Z_o$ for each signal line 15, the attenuation constant and the overall length.

In the above-mentioned electronscopes 3a and 3b, as the lengths of the insertion parts 2a and 2b are different from each other, if the universal cords 8a and 8b are made equal to each other in length, when the signal cables 12a and 12b are inserted respectively, through the universal cords 8a and 8b the same as through the insertion parts 2a and 2b, the overall lengths of the signal cables 12a and 12b will be different from each other. However, in the first embodiment, the lengths of both signal cables 12a and 12b are made equal to each other, as shown in FIG. 1, by making the cable straight in the longer cord 8a and by looping the cable in the shorter cord 8b.

The CCU 5 provided with the above mentioned connector receiver 4 can transmit signals through the signal cable 12a or 12b with the SID 11, video signal processing circuit 21 and SID driving circuit 22.

A matching circuit 23 is interposed between the above mentioned connector receiver 4 and the video signal processing circuit 21 and SID driving circuit 22 so that, in case the connector 13 and connector receiver 4 are connected with each other, the impedance transmitting the signal without reflecting may be matched. The attenuation depending generally on the frequency in the case of transmitting an output signal through both signal cables 12a and 12b is compensated by stressing the high range side within the matching circuit 23 or video signal processing circuit 21.

As the length of the signal cables 12a and 12b are made equal to each other for the different electronscopes 3a and 3b, the above mentioned matching circuit 23 can be used in common with the CCU 5 (without being provided for each electronscope).

The above mentioned signal cable 12a or 12b made by bundling a pluraltiy of signal lines 12 into one cable is linearly inserted through the insertion part 2a or 2b.

Figure 4:
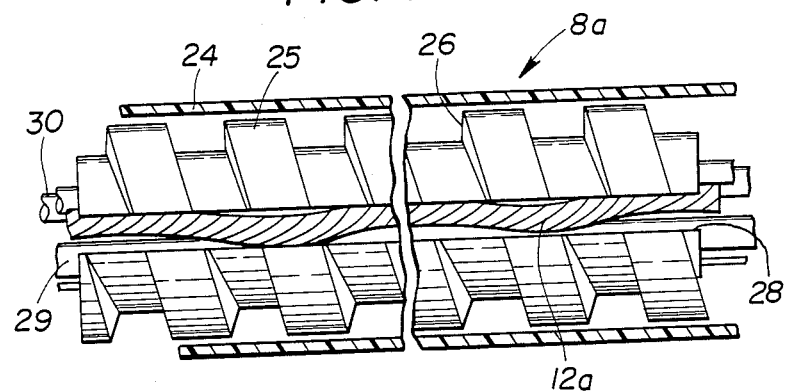

As shown in FIG. 4, the signal cable is linearly inserted through the universal cord 8a in the electronscope 3a having the long insertion part 2a. On the other hand, as shown in FIGS. 2 and 3, in order to eliminate the difference between the lengths of both signal cables 12a and 12b within the insertion parts 2a and 2b, the signal cable part corresponding to the difference in the length is wound (spirally wound in the first embodiment) to make the overall lengths of both signal cables 12a and 12b equal to each other in inserting the signal cord 8a through the electronscope 3b having the short insertion part 2b.

As shown in FIG. 2, the univeral cord 8b is covered with such sleeve 24 as of a synthetic resin and a spiral tube 25 molded of such flexible material as foaming polyurethane is fitted inside the sleeve 24. A spiral groove 26 is formed on the outer peripheral surface of this spiral tube 25 and an incision 28 communicating with an inside hollow part 27 is formed in the lengthwise direction in one place on outer peripheral surface. As shown in FIG. 3, the cross-section of this spiral tube is C-ring-shaped.

The above mentioned signal cable 12b is spirally wound along the spiral groove 26 formed on the outer peripheral surface of the spiral tube 25. This spiral part is made to be of a length compensating the difference between the lengths of the insertion parts 2a and 2b. Therefore, for example, on the insertion part 2b side, the signal cable 12b is inserted through the hollow part 27 of the spiral tube 25, is then wound along the spiral groove 26 through the incision 28 so as to be wound by the difference between the lengths of the above mentioned insertion parts 2a and 2b and is then again inserted throught the hollow part 27. Thus, the overall length of the signal cable 12a passed through the insertion part 2a and universal cord 8a in the electronscope 3a having the long insertion part 2a and the overall length of the signal cable 12 passed spirally a predetermined number of times through the short insertion as foaming polyurethane is fitted inside the sleeve 24. A spiral groove 26 is formed on the outer peripheral surface of spiral tube 25 and an incision 28 communicating with an inside hollow part 27 is formed in the lengthwise direction in one place on outer peripheral surface. As shown in FIG. 3, the cross-section of this spiral tube is C-ring-shaped.

The above mentioned signal cable 12b is spirally wound along the spiral groove 26 formed on the outer peripheral surface of the spiral tube 25 and is made to be of a length compensating the difference between the lengths of the insertion parts 2a and 2b. Therefore, for example, on the insertion part 2b side, the signal cable 12b is inserted through the hollow part 27 of the spiral tube 25, is then wound along the spiral groove 26 through the incision 28 so as to be wound by the difference between the lengths of the above mentioned insertion parts 2a and 2b and is then again inserted through the hollow part 27. Thus, the overall length of the signal cable 12a passed through the insertion part 2a and univeral cord 8a in the electronscope 3a having the long insertion part 2a and the overall length of the signal cable passed spirally a predetermined number of times through the short insertion part 8b and universal cord 8b are made equal to each other. (In electronscope 3a having the long insertion part 2a, the signal cable 12a is passed substantially linearly through the universal cord 8a as shown in FIG. 4 but. In case the signal cable 12a is longer than the universal cord 8a, a part of the signal cable 12a may be made spiral.

In the above mentioned spiral groove 26, the spacing of the adjacent grooves 26 is not made too close. That is to say, the spacing is made sufficiently large so that the reactance component in the case of making the signal cable 12a spiral may have no influence on the high range side frequency in the transmitted signal or the frequency of the driving pulses put out of the SID driving circuit 22.

A light guide 29 formed of a flexible fiber bundle and covered with a soft tube and an air and water feeding tube 30 are inserted through the hollow part 27 of the above mentioned universal cord 8a or 8b. The above mentioned light guide 29 is to transmit an illuminating light and is inserted also through the insertion part 2b (or 2a) (but is omitted in FIG. 1). When the connector 13 is connected to the connector receiver 4 of the CCU 5, a light guide connector (not illustrated) will be simultaneously connected and the light guide 29 within the universal cord 8a or 8b will be fed with an illuminating light by a light source device (not illustrated) contained in the CCU 5 so that the illuminating light may be emitted from the end surface on the tip side of the insertion part 2a (or 2b) to illuminate the object side which can be imaged by the imaging means.

The water and air feeding tube 30 is connected at one end to an air and water feeding nozzle (not illustrated) provided as opposed to the objective 9 at the tip of the insertion part 2a or 2b and at the other end to an air and water feeding pump (not illustrated) provided within the camera controlling unit 5 so that air and water may be fed to the objective.

The the above mentioned operating part 7 is provided with a curving operation knob (not illustrated) so that, by rotating the knob, a curvable part formed near the tip of the insertion part 2a or 2b may be curved to change the observing direction or bent to be inserted into an inserting path.

According to the first embodiment, as shown in FIG. 1, even if either of the electronscopes 3a and 3b, in which the lengths of the insertion parts 2a and 2b are different from each other, the lengths of the universal cords 8a and 8b are made equal to each other is connected with the CCU 5. Because the lenghts of the signal cables between the SID 11 and CCU 5 are made equal to each other, the characteristics of the output signal put into the CCU 5 will be uniformed. Therefore, it is not necessary to adjust the output characteristics for each electronscope. An endoscope device wherein the characteristics of the output signal are uniformed and the quality is constant is realized.

No matching means is required for each electronscope, a matching means can be used which common and the cost is reduced.

Two electronscopes in which the lengths of the insertion parts 2a and 2b are different from each other are mentioned in the above mentioned first embodiment. Further, in electronscopes wherein the lengths of the insertion parts are different from each other, the same output characteristics can be arranged by varying the number of times of the spiral winding.

Further, as the signal cable 12b within the above mentioned universal cord 8b is made spiral, even if this universal cord 8a is bent, the fatigue from the bending can be reduced.

In the above mentioned first embodiment, the incision 28 is provided in the peripheral direction in one place but a plurality of incisions may be provided at regular intervals along the spiral groove 26 so as to finely adjust the length of the spiral part.

As a coaxial cable is used for the signal line 15, the generation of the reactance component can be made less than in using a single line.

Without using the spiral tube 25, the signal cable 12b may be wound directly on the air and water feeding tube 36 or light guide 29 or may be wound on a flexible tube applied to cover the air and water feeding tube 30 or light guide 29. Further, the signal cable 12 may be fixed as by applying a thermally shrinking tube to cover the cable.

Figure 6:
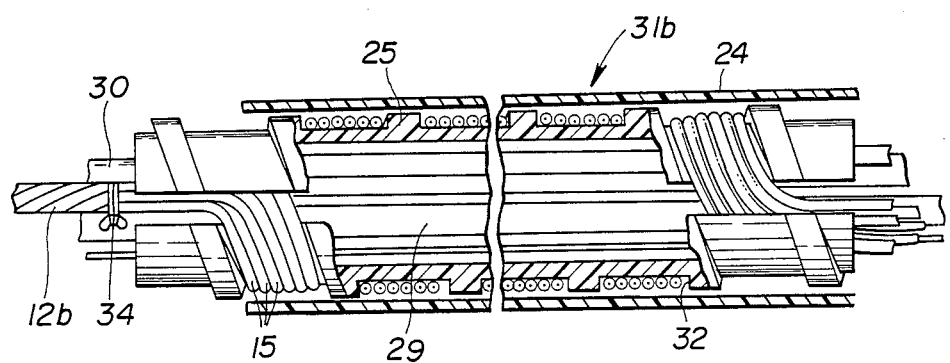
FIG. 6 is a sectioned view showing a signal cable as inserted through a universal cord in the second embodiment of the present invention.

FIG. 6 shows the structure of a universal cord in the second embodiment of the present invention.

In a univeral cord 31b of second embodiment, the depth of a spiral groove 32 formed on the outer peripheral surface of the spiral tube 25 is made small. This depth is made somewhat larger than the outside diameter of each signal line 15 of the signal cable 12b. The width of the groove 32 is made somewhat wider than the width in case the signal cable 12b is arranged in a row in the form of a flat cable. In case the signal cable 12b longer than the overall length of this universal cord 31b is to be inserted through the universal cord 31b, for example, a thread 34 as wound and bundled is passed through the hollow part 27 on the operating part side, is wound in the form of a flat cable in the spiral groove 32 and is passed as divided through the hollow part 27 on the connector side.

The others are of the same structure as in the above mentioned first embodiment.

According to this second embodiment, the operations and effects are the same as in the first embodiment and the smaller the depth of the groove 32, the smaller the outside diameter of the universal cord. If the universal cord can be made thin, it will be easy to bend and the searching property will be improved.

In this second embodiment, by reversing the winding direction of the groove 32 of the spiral tube 25 and the winding direction of the signal cable 12b to each other, the groove 32 will be able to be prevented from holding and hurting the signal cable 12b.

Figure 7:
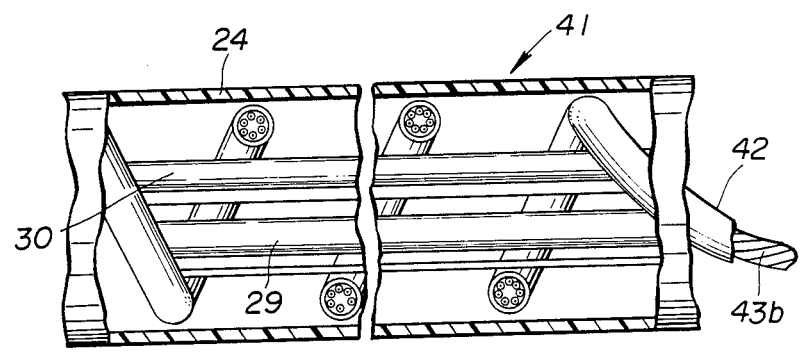
FIG. 7 is a sectioned view showing a signal cable as inserted through a universal cord in the third embodiment of the present invention.

FIG. 7 shows the structure of a universal cord 41 in the third embodiment of the present invention.

In this third embodiment, a signal cable 43b bundled as in the first embodiment is inserted through a tube (or a spirally wound tube) 42 spirally formed in advance.

In the above mentioned spirally wound tube 42, the outside diameter D of the spirally wound part is slightly smaller than the inside diameter of the sleeve 21 and such contents as the light guide 29 are passed inside this spiral winding.

The above mentioned spirally wound tube 42 is made of such material as, for example, polyurethane or tetrafluoroethylene (Teflon is famous as a produce), has a proper rigidity so that, in case the universal cord 41 is moved, even if the spiral form is deformed, it will not become so coarse and has such flexibility as will not obstruct bending.

The spirally wound tube 42 may be coated on the outer peripheral surface or inner peripheral surface with a metal film so as to be a shielded tube more positively preventing noise from mixing into the inside signal cable 43b. (Each signal line 15 of the signal cable 43b is formed of a shielded line so as to prevent noise from mixing in but, by double shielding the line, noise can be more positively prevented from mixing in.)

In this embodiment the operations and effects are the same as in the first embodiment. Further, as the spirally wound tube 42 can be cut in any position, any excess length of the signal cable 43b within the universal cord 41 can be coped with. Also, as the spiral form is held at substantially regular intervals, even if the universal cord is bent, no reactance component will be generated and even a high range signal component will be able to be transmitted without accumulating waveforms.

Figure 8:
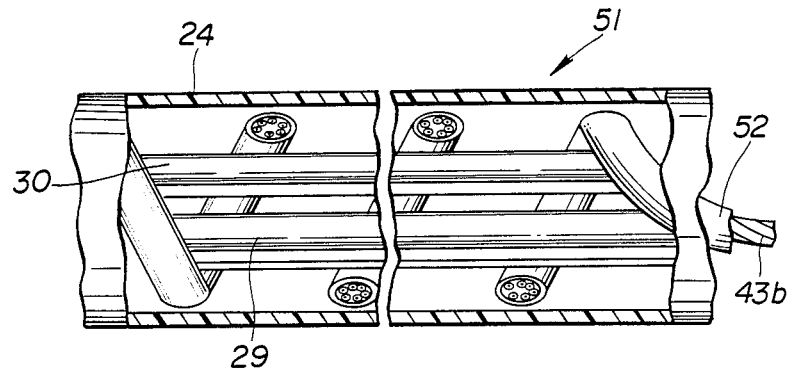
FIG. 8 is a sectioned view showing a signal cable as inserted through a universal cord in the fourth embodiment of the present invention.

FIG. 8 shows the structure of a universal cord 51 in the fourth embodiment of the present invention.

In the above mentioned third embodiment, the cross-section of the spirally wound tube 42 is a circular tube form but, in the fourth embodiment, the cross-section of the spirally wound tube 52 is an elliptic tube form.

Thereby, the outside diameter of the universal cord 51 can be made smaller.

Figure 9:
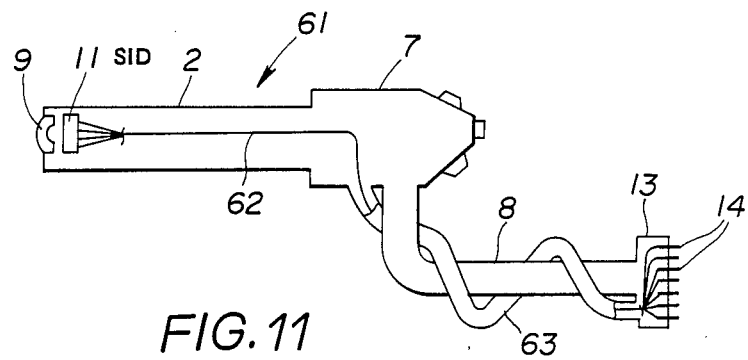
FIG. 9 is an explanatory view showing an electronscope in the fifth embodiment of the present invention.

FIG. 9 shows the fifth embodiment of the present invention.

In an electronscope 61 of this embodiment, a signal cable 62 inserted (usually the signal cable, light guide and air and water feeding tube are inserted) through the insertion part 2 is not inserted through the universal cord 8 but is inserted through a signal cable guide tube 63 extended out of the operating part 7. This guide tube 63 is wound on the outer periphery of the universal cord 8 so as to absorb the length in excess of the length of the universal cord 8. That is to say, the length of the guide tube 63 is varied in response to the difference of the length of the insertion part 2 and the number of times of winding on the outer periphery of the universal cord 8 is varied in response to the length of the guide tube 63. The flexibility of this guide tube 63 is made lower than of the universal cord 8. This guide tube 63 is fixed at one end to the operating part 7 with a bonding agent or the like and at the other end to the signal cable inserting hole part in the connector 13 at the tip of the universal cord 8. The signal cable 62 pulled out of the opening of the guide tube 63 is connected to the terminals 14.

This embodiment has the same effects as of the above mentioned first embodiment. Further, the internal structure of each universal cord 8 can be made the same even for the different length of the insertion part and can be realized by merely winding the guide tube side. That is to say, the universal tube 8 can be easily assembled without requiring to insert a spiral tube or the like into it.

FIG. 10 shows electronscopes in the sixth embodiment of the present invention.

In this embodiment, in electronscopes 72a and 72b have insertion parts 71a and 71b of different lengths. If the difference between the lengths of both insertion parts 71a and 71b is represented by 1, the length of the universal cord 73b of the electronscope 72b on the short insertion part 71b side is made longer by the length 1 than the length of the universal cord 73a of the electronscope 72a of the long insertion part 71a. Thus, even in the case of the electronscopes 72a and 72b of the insertion parts 71a and 71b of different lengths, the overall lengths of the signal cables 74a and 74b are made equal to each other.

According to this embodiment, there are the same effects as in the above mentioned first embodiment, the structure of the universal cord can be simplified and the cost can be made low.

Also, as the signal cable can be linearly contained even within the universal cord, the generation of a reactance component can be eliminated.

Figure 11:
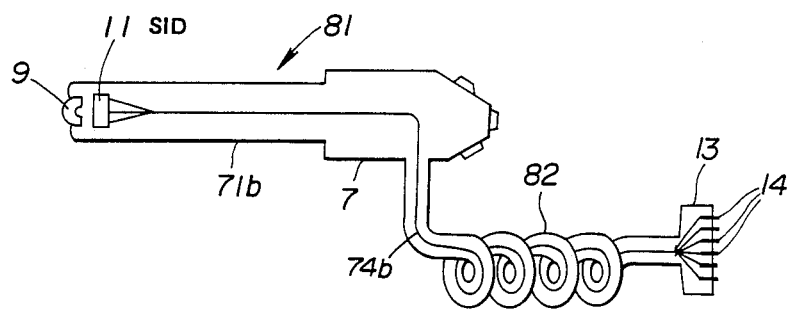
FIG. 11 is an explanatory view showing an electronscope in the seventh embodiment of the present invention.

FIG. 11 shows an electronscope of the seventh embodiment of the present invention.

In an electronscope 81 of this embodiment, a curled universal cord 81 is made by curling the long universal cord 73b, for example, in FIG. 10. Such curling is made to be of low reactance and have no influence on the signal transmitting characteristics.

In this embodiment, there are the same effects as in the above mentioned fifth embodiment. Further the universal cord 81 is curled and therefore does not obstruct the operation.

FIG. 12 shows an endoscope device 91 of the eighth embodiment of the present invention.

In an electronscope 92 forming this eighth embodiment, in order that a signal cable 93b may be of a length equal to the length of the signal cable of the other electronscope, not illustrated, as shown in FIG. 13, a snaked groove 95 is made on the outer peripheral surface of a signal cable guide tube 94 inserted through the universal cord 8. The excess length part of the signal cable 93b is contained in this snaked groove 95. The snaked groove 95 can communicate with a hollow part 97 of a guide tube 95 through an incision 96. When the signal cable 93b is passed along this snaked groove 95, the winding direction of the signal cable 93b will be reversed at a fixed period so that the generated inductance component may be made small.

In this embodiment, as shown in FIG. 12, the output of the SID 11 is amplified by a preamplifier 101 contained on the tip side of the insertion part 2b and is then put into the video signal processing circuit 21 of a CCU 5' through the signal cable. The driving pulses of the SID driving circuit 22 are put into a waveform shaping circuit 102 contained in the tip part of the insertion part through the signal cable 93b, have the waveform shaped in this circuit and are impressed on the SID 11.

The light guide 29 inserted through the insertion part 2b is inserted through the universal cord 8. By fitting this light guide 29 at the rear end to a light guide connector receiver 104 of a light source device 103 within the CCU 5', an illuminating light of a light source lamp 105 is fed through a rotary color filter 106 and lens 107. The above mentioned rotary color filter 106 is rotated and driven by a motor 108 and the illuminating light is fed in the colors of R, G and B to the light guide 29 through a three-primary color separating filter (not illustrated) of this rotary color filter 106. The driving pulses of the SID driving circuit 22 are synchronized with the rotation of this rotary color filter so that, at the time when the illuminations of R, G and B respectively finish, the driving pulses will be put out and a signal will be put out of the SID 11.

This embodiment is of a surface successively illuminating system. However, the present invention can be applied in the same manner also to a color imaging system imaging in a white light. In the case of the color imaging system in a white illumination, a color mosaic filter is arranged in front of the SID 11.

FIG. 14 shows the ninth embodiment of the present invention.

In this ninth embodiment, the invention is applied to a television camera-fitted fiberscope in which a television camera 113 is fitted to an eyepiece part 112 of a fiberscope 111.

In the above mentioned fiberscope 111, an image guide 115 and light guide 116 are inserted as image transmitting means through an insertion part 114. This image guide 115 transmits an optical image formed on the entrance end surface by an objective 117 to the end surface on the eyepiece part side so as to be able to be observed through an eyepiece 118 usually with the naked eye. The above mentioned light guide 116 is fed with an illuminating light from a light source device in a CCU 121 through a universal cord 119.

The television camera 113 fitted to the above mentioned eyepiece part 112 formes on an SID 123 an optical image transmitted by the image guide 115 through a magnifying lens 122. A signal cable 124 extended out of the television camera 113 is passed through a curled cord 125 and is connected to the CCU 121. The curled cord 125 internally fitted with this signal cable 124 is made equal in the overall length to the signal cables 12a and 12b of the electronscopes 3a and 3b of the above mentioned respective embodiments. Thus, by making the length of the signal cable 124 equal to the length of that of the other electronscope, a common matching circuit can be used and the output characteristics can be uniformed.

Figure 15:
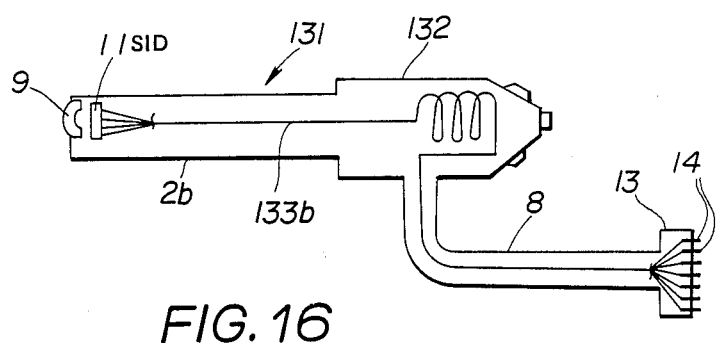
FIG. 15 is an explanatory view showing an electronscope in the tenth embodiment of the present invention.

FIG. 15 shows the tenth embodiment of the present invention.

In an electronscope 131 of this embodiment, a signal cable 133b is housed within an operating part 132 of the electronscope 131 of the insertion part 2b shorter by the difference between the lengths of the insertion parts 2a and 2b.

According to this embodiment, the effects are the same as in the above mentioned first embodiment. The structure and dimensions of the universal cord 8 can be made simple and uniform and the cost can be made low.

Figure 16:
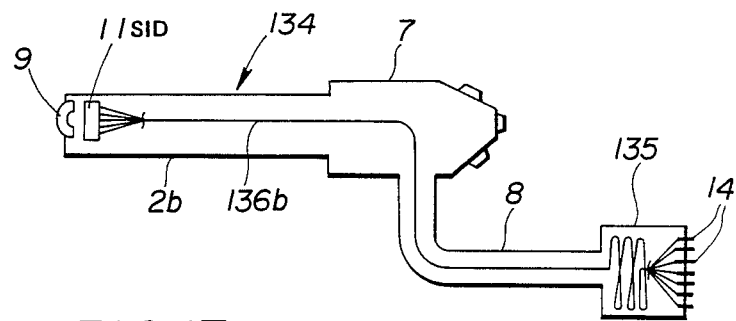
FIG. 16 is an explanatory view showing an electronscope in the eleventh embodiment of the present invention.

FIG. 16 shows the eleventh embodiment of the present invention.

In an electronscope 134 of this embodiment, a comparatively large connector 135 is provided so that a signal cable 136b may be housed within the connector 135 by the difference between the lengths of the insertion parts 2a and 2b.

According to this embodiment, the structure of the universal cord 8 is simple. The signal cable 136b housing work is shorter in the time than the work of winding the signal cable along the spiral groove 26 in the first embodiment and therefore the cost can be made lower.

Figure 17:
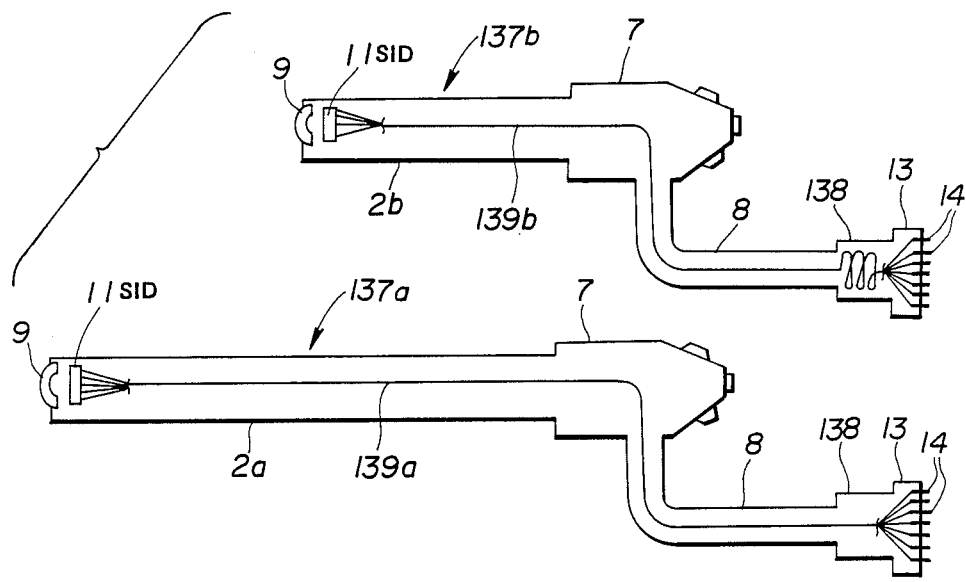
FIG. 17 is an explanatory view showing an electronscope in the twelfth embodiment of the present invention.
Figure 18:
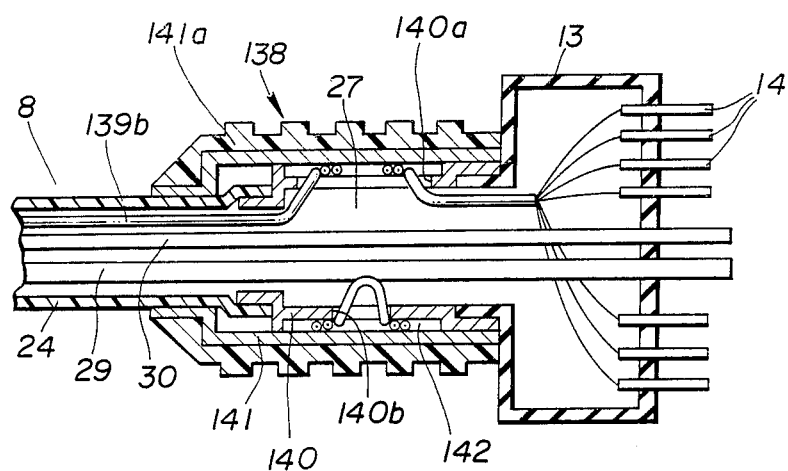
FIG. 18 is a sectioned side view of a signal cable housing part in the twelfth embodiment of the present invention.

FIGS. 17 and 18 show the twelth embodiment of the present invention.

In electronscopes 173a and 137b of this embodiment, a cable housng part 138 is provided between the universal cord 8 and connector 13 so that, in the electronscope 137b having the short insertion part 2b, a signal cable 139b may be housed by the difference between the length of the insertion parts 2a and 2b.

The cable housing part 138 comprises an inner tube 140 and outer tuber 141 and the space between the inner tube 140 and outer tube 141 is a tubular winding chamber 142. The inner tube 140 is provided with slots A140a and B140b elongated in the axial direction. The width of the slots A140a and B140b is a little wider than the signal cable 139b. The length of the slot A140a is the same as or longer than the length of the slot B140b and is a little shorter than the overall length of the winding chamber 142. The difference part between the lengths of the insertion parts 2a and 2b of the signal cable 139b is pulled out of the slot A140a and is wound as directed to the center side from both end sides of the winding chamber 142 on the outer periphery of the inner tube 140. Further, a part of the signal cable 139b can be inserted into the inner tube 140 through the slot B140b. The signal cable 139b thus wound on the inner tube 140 is fixed with a vinyl tape not illustrated. The outer tube 141 is coated with a coating rubber 141a of a form having a plurality of grooves. The light guide 29, air and water feeding tube 30 and pin-shaped terminals 14 project on the end surface of the connector 13.

According to this embodiment, the same effects as as are obtained in the above mentioned first embodiment. The structure of the universal cord 8 can be simplified and the structure of the signal cable housing part 138 is also simple. The signal cable 139b can be very simply wound on the inner tube and therefore the cost can be made low.

Further, as the signal cable 139b is wound both clockwise and counterclockwise, the inductance components will be canceled.

This signal cable housing part 138 can be used as a holding part in the case of detachably fitting the connector 13 to the camera controlling unit 5 and therefore the connector is easy to fit detachably. Further, as the signal cable housing part 138 is provided on the outer peripheray with a coating rubber 141a, the connector can be detachably fitted with a light power amount without slipping.

The signal cable housing part 138 may be provided in the couse of the universal cord 8 or between the universal cord 8 and operating part 7.

Figure 19:
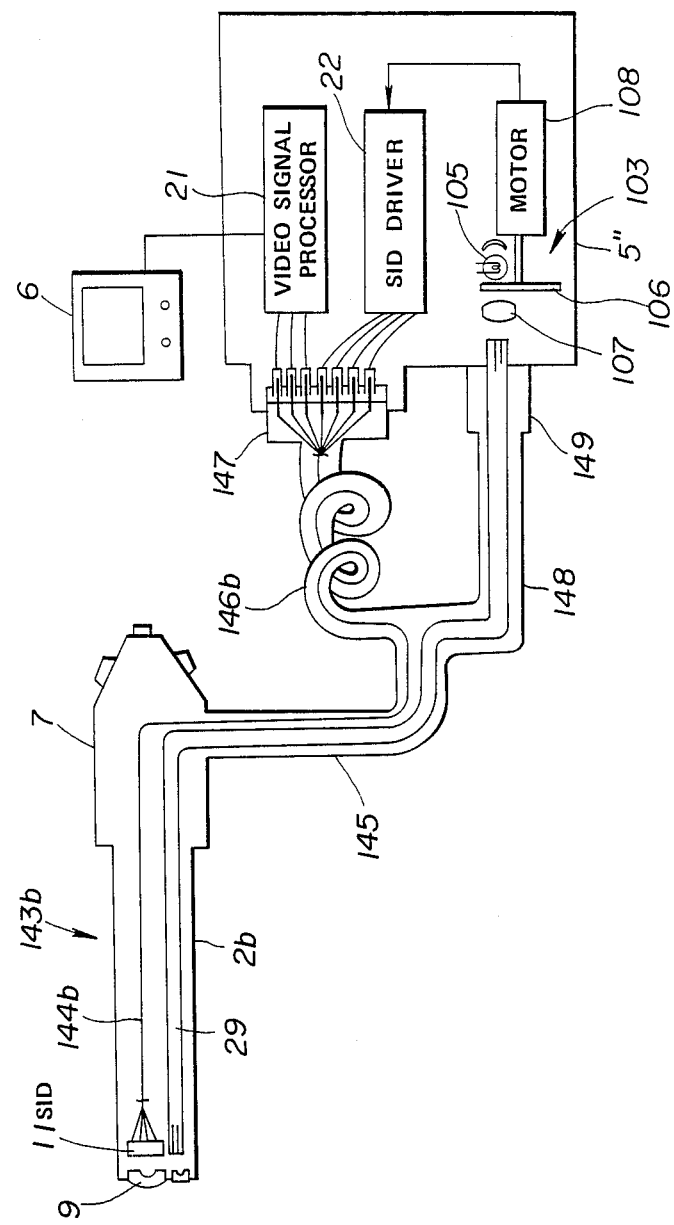
FIG. 19 is a schematic formation view of the thirteenth embodiment of the present invention.

FIG. 19 shows the thirteenth embodiment of the present invention. In an electronscope 143 of this embodiment, a universal cord 145 through which are inserted a signal cable 144, the light guide 29 and the air and water feeding tube 30 is branched into a signal cable guide cord 146 through which is inserted the signal cable 14 and a light guide cord 148 through which is inserted the light guide 29. The signal cable guide cord 146 and light guide cord 148 have at the ends respectively a signal cable connector 147 and light guide connector 149 which are respectively separately connected to the camera controlling unit 5″. The signal cable guide cord 146 is curled. The difference between the lengths of the signal cable guide cords 146a and 146b is equal to the difference between the lengths of the insertion parts 2a and 2b.

According to this embodiment, only the length of the signal cable guide cord 146 may be varied in response to the insertion part length. Therefore the structure is simple. A commercial electric connector can be used for the signal cable connector 147 and therefore the cost is low.

The air and water feeding tube 30 may be inserted through the signal cable guide cord 146. Further, the signal cable 144 may be spirally inserted through the signal cable guide cord 146.

Now, in the case of removing the reset noise components contained in the output signal, if the lengths of the signal cables are different, a delay will be produced in response to the lengths and therefore it will be necessary to delay the sampling timing. However, according to the above mentioned respective embodiments, the delay amount is constant and therefore the noise can be removed without requiring to adjust each scope.

It is natural that, even if the lengths of the signal cables are made equal to each other, some errors not substantially influencing the output characteristics will be allowed on the resistance and reactance components of the signal cables influencing the output characteristics of the SID.

In the above mentioned respective embodiments, the signal line or the like for feeding electricity in the signal cable need not be always made equal to the other signal line.

The light source device need not always be housed within the CCU 5 or 5' but may be separate. Further, without providing the light source device, such illuminating light generating means as an LED or lamp may be provided at the tip of the insertion part. That is to say, an illuminating means may be at the tip of the insertion part.

By the way, the groove 95 of the guide tube 96 in FIG. 13 may be made shallow and the signal cable may be housed in the form of a flat cable or in the form of a flat bundled cable. Also, without forming the signal cable housing groove, the signal cable may be fixed with a bonding agent or the like on the outer peripheral surface of a circular tubular form.

The other embodiments formed by partly combining the above described respective embodiments belong to the present invention.

The parts not explained in the respective embodiments are equal to the structures of the first embodiment and other embodiments.

The universal cord and signal cable side cord are generally called signal cable cords.

What is claimed is:

1. An endoscope device comprising:
    two kinds of electronscopes different at least in the length of the insertion part and each provided with an insertion part elongated so as to be insertable into a body cavity or the like, a solid state imaging device having its imaging surface having a photoelectric converting function arranged in the focal plane of an objective arranged on the tip side of said insertion part and forming an imaging means together with said objective and an illuminating means provided at the tip of said insertion part;
    a camera controlling unit housing a solid state imaging device driving circuit generating driving pulses for reading out signals in said solid state imaging device and a video signal processing means taking in and processing the output signal put out of the solid state imaging device by impressing said driving pulses;
    a monitor means displaying as a picture image the video signal put out of said video processing means; and
    a signal cable connecting said solid state imaging device and camera controlling unit with each other, transmitting said driving pulses and output signals and made to be of a fixed length irrespective of the length of the insertion part of said electronscope.

2. An endoscope device according to claim 1 wherein, in case the length of said insertion part is different, said signal cable is extended from said electronscope at least for the short insertion part and is spirally wound at least in a part within a signal cable cord provided with a connector detachably fitted to said camera controlling unit.

3. An endoscope device according to claim 2 wherein said signal cable cord has a guide member spirally defining and holding said signal cable.

4. An endoscope device according to claim 1 wherein said signal cable cord extended from said electronscope and provided with a connector detachably fitted to said camera controlling unit linearly houses said signal cable and is of a fixed length of the sum of the length of the insertion part and the length of the signal cable cord.

5. An endoscope device according to claim 1 wherein said signal cable is extended out of the rear end side of the insertion part, connects said electronscope and said camera controlling unit with each other and is spirally wound to be of a fixed length on the outer periphery of a universal cord containing an air and water feeding tube or the like.

6. An endoscope device according to claims 2, 3 or 5 wherein the spiral pitch intervals of said signal cable are made coarse in response to the maximum frequency of transmitted signals of the signal cable.

7. An endoscope device according to claim 3 wherein said guide member reverses the spiral winding direction of the housing part of the signal cable and the spiral winding direction of the signal cable with each other.

8. An endoscope device according to claim 1 wherein the spiral winding direction for the signal cable in the electronscope of at least the short insertion part is made reverse at a fixed period for the electronscope of the long insertion part.

9. An endoscope device according to claims 2, 3 or 8 wherein said signal cable is made by circularly bundling a plurality of signal lines forming said signal cable.

10. An endoscope device according to claims 2, 3 or 8 wherein said signal cable is made by arranging a plurality of signal lines forming said signal cable so as to be in a flat form.

11. An endoscope device according to claim 1 wherein said signal cable is housed within a signal cable housing part provided in the elecronscope.

12. An endoscope device according to claim 11 wherein said cable housing part is provided between the signal cord extended from said electronscope and the connector detachably fitted to said camera controlling unit.

13. An endoscope device according to claim 11 wherein the signal cable is wound on a cylindrical winding chamber provided within the signal cable housing part.

14. An endoscope device according to claim 13 wherein the signal cable is wound both clockwise and counterclockwise and the winding lengths are equal to each other.

15. An endoscope device comprising:
an electronscope provided with an insertion part elongated so as to be insertable into a body cavity or the like, a solid state imaging device having its imaging surface having a photoelectric converting function arranged in the focal plane of an objective arranged on the tip side of said insertion part and forming an imaging means together with said objective and an illuminating means provided at the tip of said insertion part;

a fiberscope provided with an insertion part elongated so as to be insertable into a body cavity or the like, an optical transmitting means arranged so that one end surface may face the focal plane of an objective arranged on the tip side of said insertion part and transmitting an optical image to the other end surface facing the eyepiece part side through the insertion part, an eyepiece part making the optical image transmitted by said optical image transmitting means observable through the eyepiece and an illuminating means provided at the tip of said insertion part;

a television camera provided with a fitting means to the eyepiece part of said fiberscope, an image forming lens for said transmitted optical image and a solid state imaging device having the imaging surface having a photoelectric converting function arranged in the focal plane of said image forming lens and forming an imaging means together with said image foming lens;

a camera controlling unit housing a solid state imaging device driving circuit electrically connectable with said electronscope or television camera and generating driving pulses for reading out signals in said solid state imaging device and a video signal processing means taking in and processing the output signal put out of the solid state imaging device by impressing said driving pulses;

a monitor means displaying as a picture image the video signal put out of said video signal processing means;

a signal cable connecting the solid state imaging device of said electronscope and said camera controlling unit with each other and transmitting said driving pulses and output signals; and a signal cable connecting the solid state imaging device of said television camera and said camera controlling unit with each other and having a length equal to that of the above mentioned signal cable.

16. An endoscope device according to claim 15 wherein said electronscope consists of the first and second electronscopes different in the length of the insertion part and the lengths of said signal cables are equal to each other.

17. An endoscope device according to claim 4 wherein at least a part of said signal cable cord is formed to be spiral.

* * * * *